US012797523B2

(12) United States Patent
Patel et al.

(10) Patent No.: US 12,797,523 B2
(45) Date of Patent: Nov. 17, 2026

(54) DIALYSIS SYSTEM HAVING REMOTE MONITORING AND CONTROL

(71) Applicant: Outset Medical, Inc., San Jose, CA (US)

(72) Inventors: Bhavesh Patel, Union City, CA (US); Mike Donnelly, San Jose, CA (US); Chetna Priyadarshini, Pflugerville, TX (US); Aaron Carrano, San Jose, CA (US); Tanuj Chirmar, San Jose, CA (US); Julie Berry, Portland, OR (US); Kaya Alpan, Palo Alto, CA (US); Elaine Brogna Cavalier, Los Gatos, CA (US)

(73) Assignee: Outset Medical, Inc., San Jose, CA (US)

( * ) Notice: Subject to any disclaimer, the term of this patent is extended or adjusted under 35 U.S.C. 154(b) by 689 days.

(21) Appl. No.: 17/485,249

(22) PCT Filed: Sep. 15, 2021

(86) PCT No.: PCT/US2021/050562
§ 371 (c)(1),
(2) Date: Sep. 24, 2021

(87) PCT Pub. No.: WO2023/043441
PCT Pub. Date: Mar. 23, 2023

(65) Prior Publication Data
US 2024/0100232 A1 Mar. 28, 2024

(51) Int. Cl.
*A61M 1/16* (2006.01)
*A61M 1/14* (2006.01)

(52) U.S. Cl.
CPC ............ *A61M 1/1601* (2014.02); *A61M 1/14* (2013.01); *A61M 2205/3331* (2013.01)

(58) Field of Classification Search
CPC ...... A61M 2205/3331; A61M 2205/35; A61M 2205/331; A61M 2205/50
See application file for complete search history.

(56) References Cited

U.S. PATENT DOCUMENTS

| | | | | |
|---|---|---|---|---|
| 2004/0143741 A1* | 7/2004 | Edwards | G06Q 20/341 713/176 |
| 2005/0078082 A1* | 4/2005 | Muralidharan | A61B 6/548 345/156 |

(Continued)

FOREIGN PATENT DOCUMENTS

| | | | |
|---|---|---|---|
| CN | 101394875 | * 3/2009 | A61M 1/16 |
| CN | 109069777 | * 12/2018 | A61M 16/0063 |

*Primary Examiner* — Rebecca E Eisenberg
*Assistant Examiner* — Matthew Wrubleski

(57) ABSTRACT

A dialysis system includes a fluidics system configured to perform a dialysis treatment session for a patient by having sensor(s) that measure corresponding parameter(s) and having dialysis actuator(s) that configures fluid flow through the fluidics system. The dialysis system includes a communication subsystem configured to communicatively connect to user device(s). A controller of the dialysis system is communicatively coupled to the fluidics system and the communication subsystem. The controller operates the fluidics system to perform the dialysis treatment session. The controller maintains data associated with the fluidics system. The data includes data types of patient health information, de-identified health information; and non-health information. The controller identifies access rights associated with first credential used by a first user device to the data types and communicates the data types to the first user device according to the access rights.

17 Claims, 9 Drawing Sheets

(56) References Cited

U.S. PATENT DOCUMENTS

| | | | | |
|---|---|---|---|---|
| 2005/0126961 | A1* | 6/2005 | Bissler | A61M 1/3639<br>210/97 |
| 2008/0103447 | A1* | 5/2008 | Reggiardo | H04W 12/08<br>604/131 |
| 2011/0189048 | A1* | 8/2011 | Curtis | A61M 1/1656<br>210/85 |
| 2012/0253157 | A1* | 10/2012 | Yamaguchi | A61B 1/0646<br>600/328 |
| 2013/0274642 | A1* | 10/2013 | Soykan | A61B 5/389<br>604/5.01 |
| 2016/0058933 | A1* | 3/2016 | Ballantyne | G06F 21/565<br>210/85 |
| 2016/0206800 | A1* | 7/2016 | Tanenbaum | A61M 1/1613 |
| 2016/0250406 | A1* | 9/2016 | Parisotto | A61M 1/3659<br>210/646 |
| 2020/0051244 | A1* | 2/2020 | Hanina | G16H 20/17 |

* cited by examiner

DIALYSIS SYSTEM HAVING REMOTE MONITORING AND CONTROL

TECHNICAL FIELD

The present disclosure relates generally to dialysis systems, and more particularly, to systems and methods for remotely monitoring and controlling a dialysis system during a dialysis treatment.

BACKGROUND

There are, at present, hundreds of thousands of patients in the United States with end stage renal disease. Patients experiencing kidney failure require dialysis or a kidney transplant to survive. Many patients receive dialysis treatment at a dialysis center, which can place a demanding, restrictive, and tiring schedule on a patient. Patients who receive in-center dialysis typically must travel to the center at least three times a week where they are required to sit in a chair for at least 3 to 4 hours each time while toxins and excess fluids are filtered from their blood. Some treatments can last for 8-12 hours or even longer. Most patients must travel to and from a dialysis center in order to receive dialysis treatments from highly trained medical professionals such as physicians and nurses that are knowledgeable and skilled at configuring and operating highly complex dialysis machines, and who are readily available to address problems with a particular dialysis treatment or to adjust treatment parameters and prescriptions for ongoing treatments in real time. After the treatment, the patient must wait for the venous access site to stop bleeding and blood pressure to return to normal, which requires even more time taken away from other, more fulfilling activities in their daily lives. Moreover, in-center patients must follow an uncompromising schedule as a typical center treats three to five shifts of patients in the course of a day. As a result, many people who dialyze multiple times per week are frustrated and complain of feeling exhausted for at least a several hours after each dialysis session.

The operation of many dialysis systems on the market requires significant medical and technical knowledge and skill to configure and operate, and attention from technicians prior to, during, and after a dialysis treatment. For example, prior to administering a treatment, technicians are often required to manually install patient blood tubing sets onto the dialysis system, connect the patient to the dialysis machine through intravenous (IV) cannulation, and manually prime the tubing sets to remove air from the tubing set before therapy. During therapy, the healthcare providers are typically required to monitor the patient's vitals, to monitor venous pressure and fluid levels of the dialysis machine during its operation, and to provide therapeutic actions such as administering required medications or providing boluses of saline and/or heparin to the patient to alleviate their physical discomfort and protect the patient's health. After therapy, technicians must return blood remaining in the tubing set to the patient, drain the dialysis system, and collect and record the patient's vitals and the results of a treatment. The inefficiencies of most dialysis systems and the need for significant technician involvement in the process make it even more difficult for patients to receive dialysis therapy away from large treatment centers.

Given the demanding and inconvenient nature of in-center dialysis, many patients have turned to home-based dialysis as an option. Home-based dialysis can provide patients with scheduling flexibility as it permits the patient to choose treatment times to fit other activities and eliminates the need for the patient to travel to and from dialysis treatment centers to undergo treatment. Home dialysis systems, particularly home-based hemodialysis systems, are available but generally require a skilled healthcare technician or care partner be physically present throughout the dialysis treatment to administer the treatment, and to handle adjustments and potential system alerts or errors that the patient may not possess the medical, technical, or physical skills or abilities to handle on their own. Frequently, a care partner may not be a professionally trained physician or nurse, but a family member, spouse, or friend of the patient. In some instances, it may be possible for a dialysis technician to configure and initiate a dialysis treatment in-home, after which the potentially unskilled care partners must be present throughout the entirety of each lengthy treatment session where they simply wait for, and potentially respond to, alerts that may occur during a treatment session. Whether treatment is administered and/or monitored by a dialysis technician or a care partner, the lengthy time commitment is a substantial inconvenience, not only for the patient, but for the dialysis technician and/or care partner. Further, where required, an unskilled care partner can find it challenging to interact with a dialysis system having potentially complex alerts and a user interface designed for medically experienced professionals to operate. The present innovation addresses this and other deficiencies in conventional dialysis systems.

SUMMARY

In one aspect of the present disclosure, a dialysis system includes a fluidics system configured to perform a dialysis treatment session for a patient, the fluidics system comprising: (i) at least one sensor that senses a corresponding at least one parameter; and (ii) at least one dialysis actuator that configures fluid flow through the fluidics system. The dialysis system includes a communication subsystem configured to communicatively connect to one or more user devices. The dialysis system includes a controller communicatively coupled to the fluidics system and the communication subsystem. The controller operates the fluidics system to perform the dialysis treatment session. The controller maintains data associated with the fluidics system, the data comprising data types of at least two of: (i) patient health information (PHI); (ii) de-identified health information; and (iii) non-health information. Non-health information can be technical information and other types of information that does not contain PHI. The controller identifies access rights associated with a first credential used by a first user device to one or more of the data types. The controller communicates one or more of the data types to the first user device according to the access rights. In response to receiving a control input from the first user device, the controller identifies control privileges associated with the first credential used by the first user device to reconfigure the fluidics system to change the dialysis treatment session, the control privileges being stratified into control levels of: (i) no control allowed; (ii) limited control; and (iii) full control. The controller monitors the at least one sensor and respective states of the more than one fluidics actuators to determine a current state of the dialysis treatment session. The controller determines whether the control input is therapeutically allowed based on the current status of the dialysis treatment session. The controller determines whether the first user device has the corresponding control level associated with the control input. The controller configures the fluidics system in response to the control input being both allowed therapeutically and according to control level.

In another aspect of the present disclosure, a dialysis system includes a fluidics system configured to perform a dialysis treatment session for a patient, the fluidics system comprising: (i) at least one sensor that senses a corresponding at least one parameter; and (ii) at least one dialysis actuator that configures fluid flow through the fluidics system. The dialysis system includes a communication subsystem configured to communicatively connect to one or more user devices. The dialysis system includes a controller that is communicatively coupled to the fluidics system and the communication subsystem. The controller operates the fluidics system to perform the dialysis treatment session. The controller maintains data associated with the fluidics system, the data comprising data types of at least two of: (i) PHI; (ii) de-identified health information; and (iii) non-health information. The controller identifies access rights associated with a first credential used by a first user device to one or more of the data types. The controller communicates one or more of the data types to the first user device according to the access rights.

In an additional aspect of the present disclosure, a dialysis system includes a fluidics system configured to perform a dialysis treatment session for a patient. The fluidics system includes at least one sensor that measure corresponding at least one parameter and includes at least one dialysis actuator that configures or reconfigures fluid flow through the fluidics system. The dialysis system includes a communication subsystem configured to communicatively connect to one or more user devices. A controller is communicatively coupled to the fluidics system and the communication subsystem. The controller operates the fluidics system to perform the dialysis treatment session. In response to receiving a control input from the first user device, the controller identifies control privileges associated with the first credential used by the first user device to reconfigure the fluidics system to change the dialysis treatment session, the control privileges are stratified into control levels of: (i) no control allowed; (ii) limited control; and (iii) full control. The controller monitors the at least one sensor and respective states of the more than one fluidics actuators to determine a current state of the dialysis treatment session. The controller determines whether the control input is therapeutically allowed based on the current status of the dialysis treatment session. The controller determines whether the first user device has the corresponding control level associated with the control input. The controller configures the fluidics system in response to the control input being both allowed therapeutically and according to control level.

These and other features are explained more fully in the embodiments illustrated below. It should be understood that in general the features of one embodiment also may be used in combination with features of another embodiment and that the embodiments are not intended to limit the scope of the disclosure.

BRIEF DESCRIPTION OF THE DRAWINGS

The various exemplary embodiments of the present innovation, which will become more apparent as the description proceeds, are described in the following detailed description in conjunction with the accompanying drawings, in which.

DETAILED DESCRIPTION

Figure 1A:
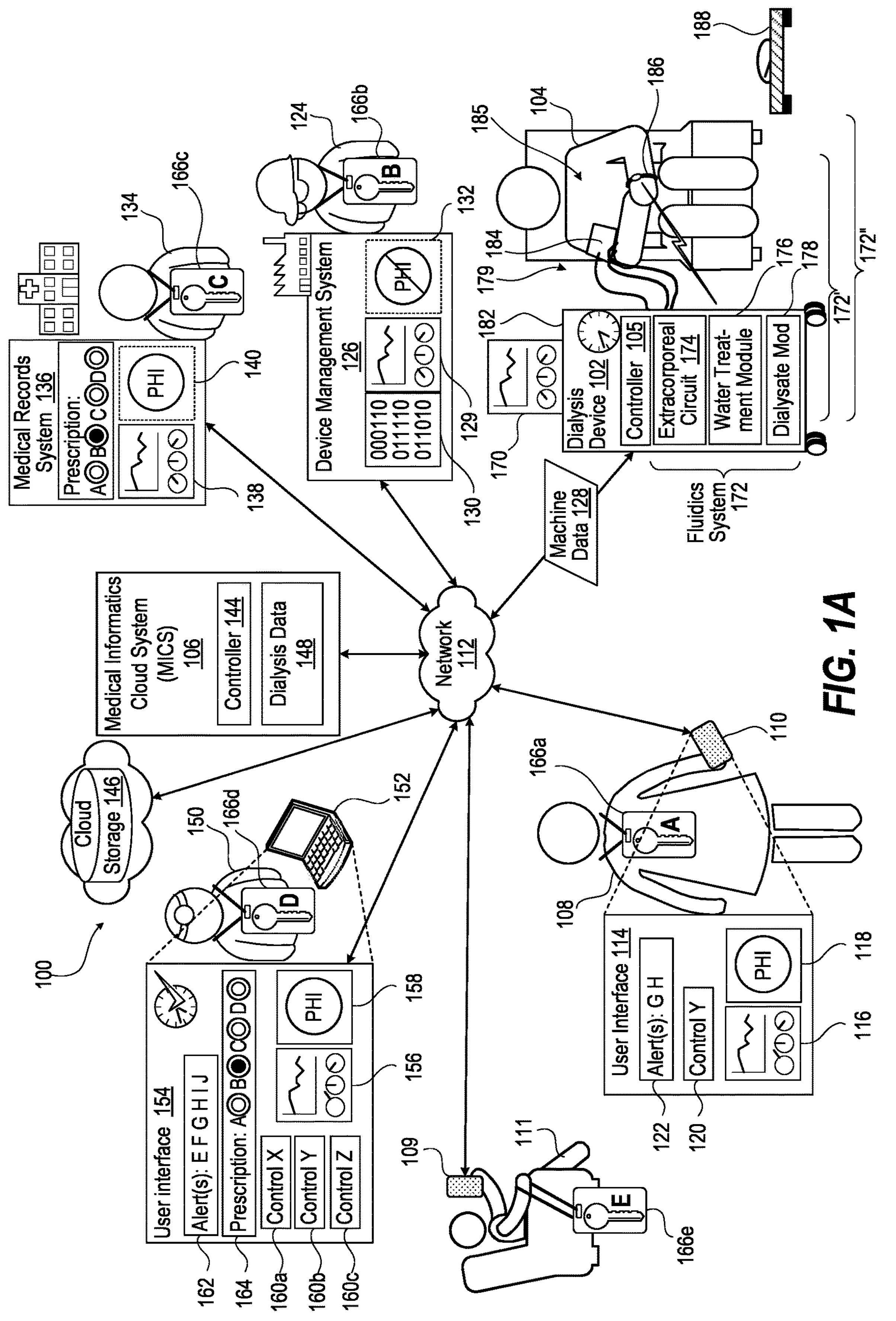
FIG. 1A is a diagrammatic illustration of an exemplary dialysis system.

FIG. 1A is a diagrammatic illustration of an exemplary dialysis system 100 that enables home use of dialysis device 102 by patient 104 for regulating the flow of dialysate and blood to and from an extracorporeal circuit 174 to achieve different types of dialysis, including hemodialysis, ultrafiltration, and hemodiafiltration. In hemodialysis, dialysis device 102 filters waste, salts, and excess fluid from the blood of patient 104 whose kidneys are no longer healthy enough to do this work adequately. In ultrafiltration, dialysis device 102 removes excess fluid from the blood of patient 104 and is one of the functions of the kidneys that dialysis treatment replaces. In hemodiafiltration, dialysis device 102 performs a combination of hemodialysis and hemofiltration either simultaneously or sequentially. Convective transport (hemofiltration) removes larger molecular weight substances and diffusive transport (hemodialysis) removes smaller molecular weight solutes. Dialysis device 102 is sufficiently portable and automatically maintained to enable use by patient 104 in a home setting. Aspects of the present disclosure also benefit use in clinics and institutions. Additional disclosure about one or more embodiments of dialysis device 102 is described in commonly owned and pending international patent application PCT/US2020/030751 entitled "Dialysis System and Methods", filed Apr. 30, 2020, and published as WO2020223500A1 on Nov. 5, 2020, the disclosure of which and any references cited therein are hereby incorporated by reference in their entirety. Dialysis device 102 is enhanced by incorporation of controller 105 that manages dialysis system 100 and also supports remote monitoring and control by one or more stakeholders while maintaining one or more safeguards.

According to aspects of the present disclosure, dialysis device 102 and communicatively coupled medical informatics cloud system (MICS) 106 of dialysis system 100 enable care partner 108 who is not necessarily medically trained to aid patient 104 with the dialysis treatment. Even if medically trained, aspects of the present disclosure mitigate or avoid human error. In particular, dialysis device 102 provides intuitive alerts and user controls appropriate for care partner 108, enabling care partner 108 to monitor a treatment and to provide appropriate assistance to patient 104 even when care partner 108 is not present in the same room or physical location with patient 104 undergoing a dialysis treatment session. For example, care partner 108 may be present at the beginning of the treatment to assist patient 104 in configuring dialysis device 102, with IV cannulation to connect patient 104 to dialysis device 102, and with initiating a dialysis treatment session. Care partner 108 may also be present at the end of the treatment to disconnect patient 104 from dialysis device 102, to assist with any required post-treatment actions on dialysis device 102 (e.g., removal and disposal of tubing and other consumables, cleaning, sterilization, etc.). In between, care partner 108 can remotely monitor or be on call to assist patient 104 during dialysis treatment. Dialysis device 102 enables care partner 108 to leave the immediate proximity of patient 104 during treatment yet be alerted in an intuitive manner via remote user device 110 when a remote or in-person action is advised.

In one or more embodiments, dialysis device 102 can alternatively push an alert to remote user device 109 used by remote care partner 111 to inform about the start, progress, and ending of a dialysis treatment session. For example, patient 104 or an in-person care partner or healthcare provider can be responsible for configuring and initiating the dialysis treatment session and remote care partner 111 may remotely monitor the dialysis treatment of patient 104. For example, in response to determining that the access rights of remote care partner 111 comprise notification of the dialysis treatment session, dialysis device 102 may communicate a report indicating initiation of the dialysis treatment session to remote user device 109 in response to beginning the dialysis treatment session. Dialysis device 102 also communicate a report indicating termination of the dialysis treatment session to remote user device 109 in response to ending the dialysis treatment session. Simple communication network 112 can enable communication between two or more of remote user devices 109-110, dialysis device 102, and MICS 106. For instance, communication network 112 may include one or more of wireless local or wide area access networks, private networks, cellular communication, wired local networks, etc. In one or more embodiments, controller 105 can form an ad hoc network, personal access network, or wireless local access network with the user device 110 within a home. In one or more embodiments, dialysis device 102 is one of a population of dialysis devices 102 that are supported by MICS 106 via communication network 112. In one or more embodiments, MICS 106 acts as intermediary between each dialysis device 102 and the stakeholders.

Figure 1B:
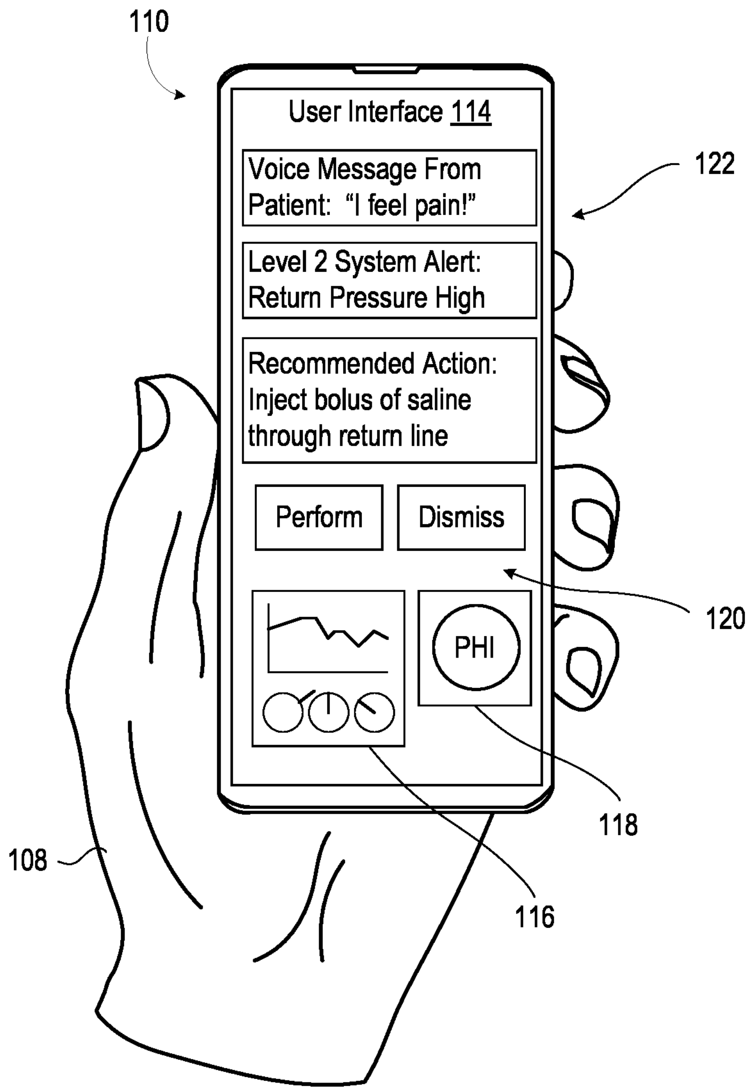
FIG. 1B is an isometric illustration of an exemplary user device held by a care partner to interact with the disclosed system of FIG. 1A.

FIG. 1B is an isometric illustration of exemplary remote user devices 109, 110 held by care partners 108, 111 to interact with dialysis system 100 (FIG. 1A). Examples of user device 110 used by care partner 108, 111 include mobile phones, tablets, laptops, desktops, kiosks, smartphones, wearables, personal digital assistants, augmented reality ("AR") devices, virtual reality ("VR") devices, etc. Care partner 108, 111 can interact with dialysis system 100 via user device 109, 110 that is capable of presenting user interface 114. Controller 105 filters presentation of data and user controls sent to user interface 114 based on the role and privileges associated with the care partner 108, 111. As an example, user interface 114 may present treatment data 116, patient health information (PHI) 118, control(s) "Y" 120, and alert(s) "G, H" 122 that are selected for a care partner. Examples of alerts 122 may include "voice message from patient: 'I feel pain!'", "Level 2 System Alert: Return Pressure High", and "Recommended Action: Inject bolus of saline through return line". Examples of controls 120 include "Perform" or "Dismiss" corresponding to a recommended action alert such as: "Inject bolus of saline through return line."

The dialysis system 100 (FIG. 1A) safeguards PHI 118, which is the most sensitive forms of patient information. The Health Insurance Portability and Accountability Act (HIPAA) of 1996 defines PHI as any information in a medical record that can be used to identify an individual and that was created, used, or disclosed in the course of providing a health care service, such as a diagnosis or treatment. Examples of PHI range from identifying information such as blood test results to billing information and can even include seemingly obscure exchanges of information, such as an email from a doctor's office. Certain stakeholders who are not entitled to have access rights to view PHI can have credentials that allow viewing de-identified health information that is less strictly protected as lacking patient identification. Examples of de-identified health information include basic data, such as sensed blood properties.

With continued reference to FIG. 1A, operation and support of dialysis device 102 can be supported by remote, role-based monitoring and control by other stakeholders via communication network 112. As an example, the stakeholders can include an agent or employee such as a biomedical engineer or field service engineer ("device technician") 124 for an original equipment manufacturer (OEM), distributor, or equipment support firm responsible for maintaining, repairing, and otherwise supporting dialysis device 102. Device technician 124 uses device management system 126 to remotely access dialysis device 102. Device technician 124 uses machine data 128 and treatment data 129 to confirm that dialysis device 102 is operating correctly and whether a maintenance action is required. Device technician 124 can use machine data 128 to provision dialysis device 102 with appropriate software and configuration settings 130. In one or more embodiments, PHI 132 is redacted from what is provided to and presented by device management system 126. As an example, a device technician 124 may be able to observe an ongoing treatment and to provide technical support during a dialysis treatment without compromising patient privacy. In one or more embodiments, controller 105 may be configured to send machine data 128 to device management system 126 for ongoing or prior treatments, and for maintenance actions taken on dialysis device 102. In one or more embodiments, controller 105. In one or more embodiments, controller 105 may be configured to send treatment data 129 to device management system 126 for ongoing or prior treatments, wherein PHI 132 is redacted from treatment data prior to sending treatment data 129 to device management system 126. In one or more embodiments, controller 105 restricts control of dialysis device 102 by device technician 124 during any ongoing or scheduled treatment. In particular, controller 105 may receive one or more signals from one or more of patient sensors 179 or fluidics system 136 sensors indicating that a patient is connected to dialysis device 102 or that a dialysis treatment session is ongoing. In response to receiving a signal indicating that patient 104 is connected to dialysis device 102, or that a dialysis treatment session is ongoing, controller 105 may be configured to automatically revoke the device technician's 124 permissions to control or perform maintenance actions on dialysis device 102. In one or more embodiments, device technician 124 may schedule over-the-air updates to dialysis device 102. Scheduled updates may be sent to dialysis device 102 from device management system 126 (e.g., from cloud storage 146) to be executed by controller 105. Controller 105 may determine that dialysis device 102 is not currently administering a treatment and that no treatment is scheduled for the anticipated duration of the update installation. Alternatively, device management system 126 or controller 105 may schedule the installation of an over-the-air update on dialysis device 102 based on a log of anticipated or scheduled dialysis treatment sessions. A schedule of dialysis treatment sessions may be stored in a variety of locations, such as, for example, directly on dialysis device 102, in device management system 126, in medical records system 136, in MICS 106, or on a user device 109, 110, or 152.

Another stakeholder is first healthcare provider 134, such as a dialysis technician, that uses medical records system 136. First healthcare provider 134, may or may not have real-time or near-real-time to dialysis treatment data 138 and PHI 140 from dialysis device 102. First healthcare provider 134 can input prescription 142 for dialysis treatment of a particular patient that is transmitted to MICS 106 and then to dialysis device 102. A specific prescription may be identified and attributed to a specific patient according to a patient identifier, which may be a unique alpha-numeric string, a hardware address or unique electrical signal belonging to a registered patient device, biometric authentication, other unique identification. Controller 105 may access and retrieve a prescription from MICS 106 according to a patient identifier. MICS 106, managed by network controller 144, can maintain data, training data, software, settings, user authentication data, etc. in cloud storage 146 for use by dialysis device 102 and the stakeholders. MICS 106 can also locally maintain dialysis data 148. Prescription 142 can define fluid removal goals and an acceptable threshold for amounts of particular contaminants or waste in the patient's blood. The vascular system of the patient can only support a certain rate of blood removal and blood return without collapsing an artery or over expanding a vein of the patient. Therefore, prescription 142 may define a period of time or a blood flow rate of dialysis expected to be comfortable or tolerable for the patient. Prescription 142 can define infusion products that are to be given to the patient. To achieve the prescription, a total blood volume of the vascular system of the patient can be sensed directly or indirectly. In an example, a patient may have a baseline "dry" weight and total blood volume. Any weight gained above this dry weight can be used to determine an amount or goal of excess fluid to be removed during treatment. Therefore, weighing the patient before and after the therapeutic session can be used to set a fluid removal goal prior to treatment, and to verify the appropriate amount of fluid was removed and/or infused during treatment to confirm that the fluid removal goal was achieved. To achieve a desired amount of filtering of wastes from the blood and a desired amount of infusing or removal of liquids, the flow rate and composition of dialysate and the flow rates of blood, drained fluid, and infused fluid may be prescribed and monitored. Over time, a rate of flow for any one of these particular liquids results in a volume of the particular liquid. When a goal is defined in terms of volume, a change in a rate of the corresponding flow results in a change in a duration of the therapeutic session. A change in the duration of the therapeutic session results in a corresponding change in the achieved volume of the particular liquid.

Figure 1C:
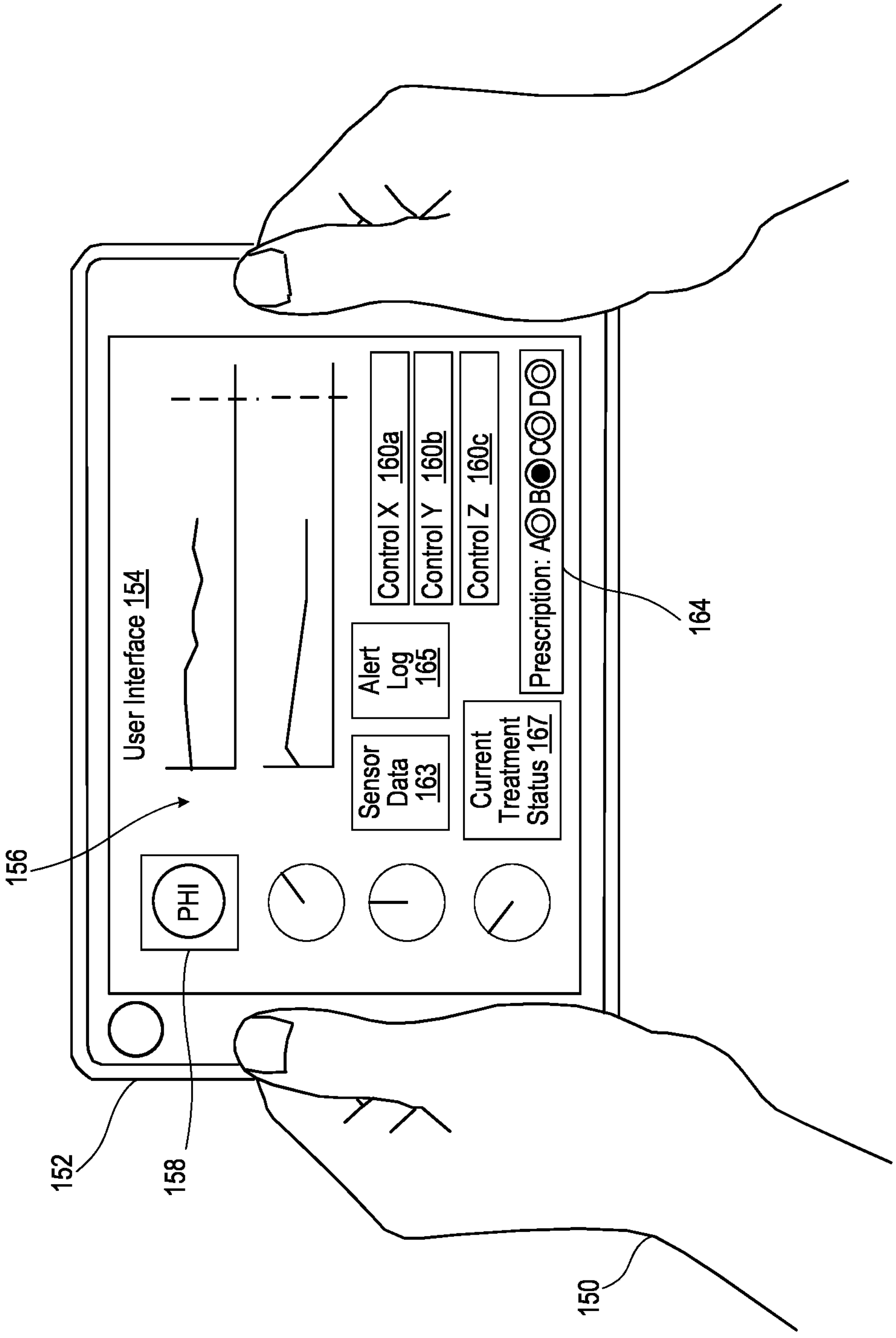
FIG. 1C is an isometric illustration of an exemplary user device held by a healthcare provider to interact with the disclosed system of FIG. 1A.

FIG. 1C is an isometric illustration of exemplary user device 152 held by second healthcare provider 150 (FIG. 1A). Second healthcare provider 150 may be granted additional access rights and control privileges over those previously discussed. For example, second healthcare provider 150 may be an additional stakeholder that is enabled by real-time monitoring and control by controller 105 to intervene via user device 152 in an ongoing dialysis treatment in real time or near real-time. In one or more embodiments, the access rights of different stakeholders may be stratified into levels of access such as: (i) all data including PHI; (ii) non-identifying treatment data; (iii) non-health technical data; and (iv) non-identifying treatment data and non-health technical data. The additional access rights and control privileges can be granted in response to one or more factors as desired. In one or more embodiments, the control privileges are stratified into levels of control such as: (i) no control; (ii) a specific subset of controls; (iii) therapeutically allowed controls; (iv) control permitted only while treatment is not ongoing, and (v) all controls. As an example, a particular stakeholder, such as a care partner may have the requisite medical training to qualify for a higher level of control that care partners 108 and 111 (FIG. 1B) would not typically be given under normal circumstances. In another example, a stakeholder may be granted specific access rights commensurate with their contractual or fiducial relationship and requisite duty of care for the patient. Having this relationship can be a precondition for a particular level of control. As an example, a user interface 154 of the user device 152 presents treatment data 156, PHI 158, controls "X, Y, Z" 160*a*-160*c*, and alert(s) "E, F, G, H, I, J" 162 that are selected for a trained medical professional. In some instances, second healthcare provider 150 can input prescription 164, or a change to the existing prescription, for dialysis treatment. In one or more embodiments, second healthcare provider 150 can be a physician's assistant or nurse that can intervene in a current treatment but requires the first healthcare provider 134 to change the prescription for future treatments so that medical records are maintained on the medical records system 136 (FIG. 1B). The user interface 154 can have a menu hierarchy including sensor data 163 and alert log 165 for detailed information. Current treatment status control 167 enables opening detailed information.

Figure 1D:
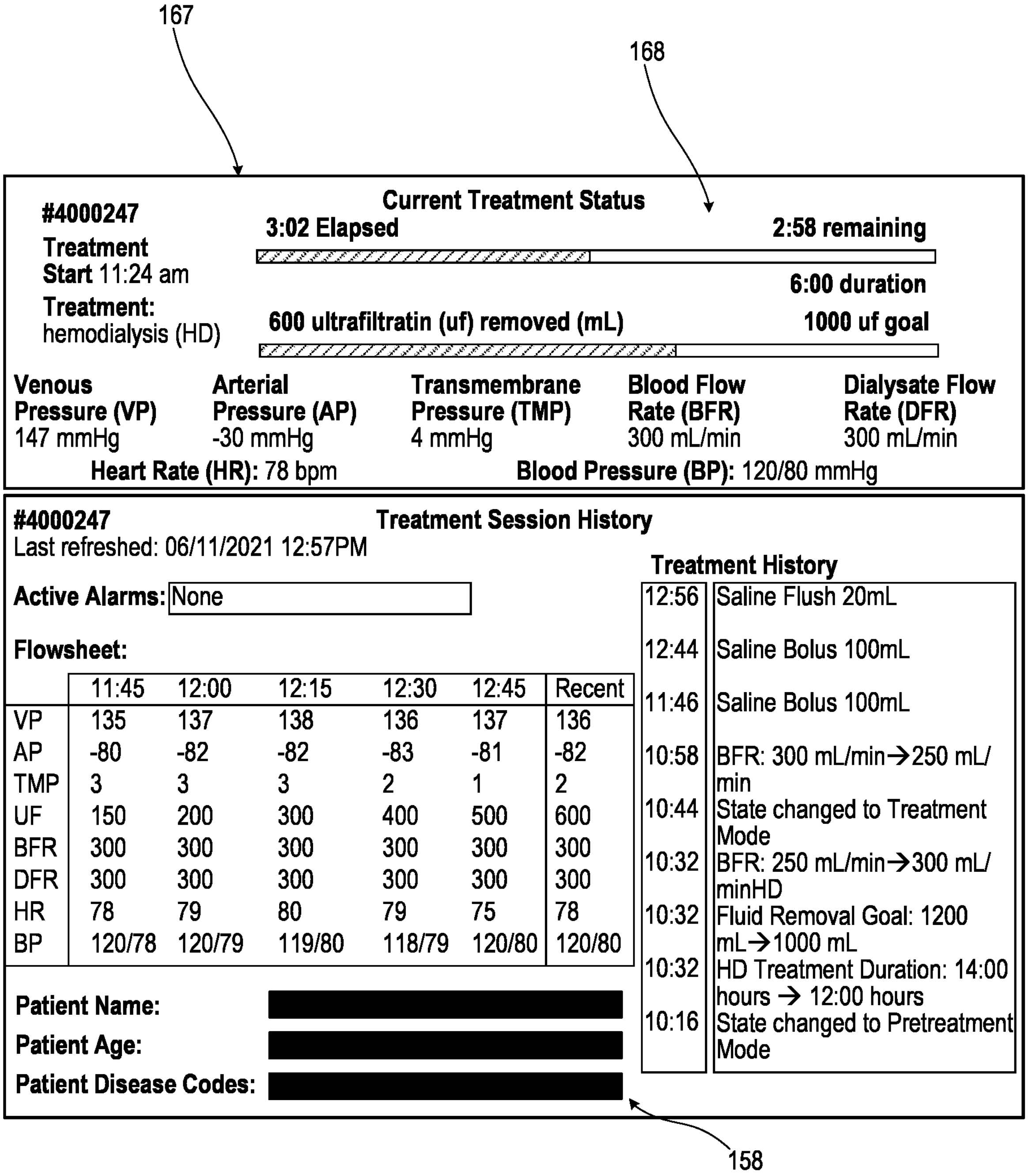
FIG. 1D is a screen shot of a graphical user interface presenting a current treatment status screen that is de-identified.

FIG. 1D is graphical user interface 154 presenting current treatment status screen 168 that is de-identified by removal of PHI 158. PHI 158 such as patient's name, patient's age, and patient's disease codes may be located at spatially-defined field locations reserved for PHI 158 on the graphical user interface 154. Alternatively, PHI 158 may be identified in a graphical user interface based on recognition of data types (e.g., JSON). PHI 158 may be redacted or obfuscated from graphical user interface 154 by controller 105 prior to transmission to a stakeholder device 109, 110, 136, or 126 to create de-identified health information in an altered graphical user interface.

In support of these different stakeholders, in FIG. 1A dialysis system 100 tracks role-based credentials "A, B, C, D, E" (166*a*-166*e*) assigned respectively to the stakeholders (108, 111, 124, 134, and 150) that confer different levels of authorization to monitor data originating at dialysis device 102. Technologies used to authenticate a stakeholder's credentials could include one or more of a biometric signature (fingerprint, eye scan, voice, facial recognition, etc.), a manually entered code, an electronic key device, an identifier for the user device used by the particular stakeholder, a radio frequency identifier (RFID) or computer access card (CAC) assigned to a stakeholder, etc. In one or more embodiments, the authentication is two-factor authentication, requiring at least two different authentication types. Role-based credentials (166*a*-166*e*) also confer different levels of authorization to configure or to control an ongoing dialysis treatment by dialysis device 102. As an example, care partners 108 and 111 as stakeholder can have role-based credentials “A” 166*a* and “E” 106*e* respectively that are appropriate for a non-medically trained person acting as a trusted caregiver to patient 104. In one or more embodiments, role-based credentials “E” 106*e* only allow corresponding stakeholder 111 to view non-PHI data. Care partners 108 and 111 are identified and authenticated by the dialysis system 100 at least in part by role-based credentials “A” 166*a* and “E” 166*e* respectively.

Each of these stakeholders can perform support for treatment sessions by the dialysis device 102 that can include local user interface device 170 for in-person monitoring and control. In one or more embodiments, controller 105 includes local user interface device 170. In additional to supporting the remote communications described above, controller 105 can support system management of fluidics system 172 that performs the dialysis treatment. Fluidics system 172 includes several modules or functional portions such as extracorporeal circuit 174, water treatment module 176, and dialysate module 178. Controller 105 senses parameters within fluidics system 172 and configures operation of fluidics system 172. Controller 105 can also receive sensor data from patient sensors 179 such as peripheral or external devices that are external to housing 182 of dialysis device 102. An example of patient sensors 179 is blood pressure cuff 184 that is configured to periodically and automatically detect systolic and diastolic blood pressure readings of vascular system 185 of patient 104. Extracorporeal circuit 174 is configured to be in fluidic communication with vascular system 185 of patient 104. Controller can also wirelessly interface to patient sensors 179 such as wearable devices 186 that are configured to detect heart rate, blood oxygen saturation, body temperature, etc., of patient 104. Patient 104 and care provider 108 can also manually obtain and enter data to controller 105 via local user interface device 170 pertinent to a dialysis treatment session using manual sensor 188, such as a weight scale that obtains beginning and ending body weight measurements. Alternatively, sensors such as sensor 188 may be configured to automatically send one or more signals to controller 105. In one or more embodiments, primary fluidics system 172 includes components integral or attachable to dialysis device 102. In one or more embodiments, expanded fluidics system 172' includes fluidics system 172 with additional patient sensing provided by one or more patient sensors 179 that are configurable to sense parameters from patient 104. In one or more embodiments, comprehensive fluidics system 172" includes expanded fluidics system 172' as well as vascular system 185 of patient 104.

In one or more embodiments, dialysis system 100 can transmit a report to remote user device 109, 110, and 152 indicating successful configuration or reconfiguration of fluidics system 172 in response to the control input being both allowed therapeutically and according to control level. Similarly, dialysis system 100 can transmit a report to remote user device 109, 110, and 152 indicating unsuccessful configuration of fluidics system 172 in response to the control input being one or more of not allowed therapeutically or not allowed according to the control associated with the credentials.

Figure 2:
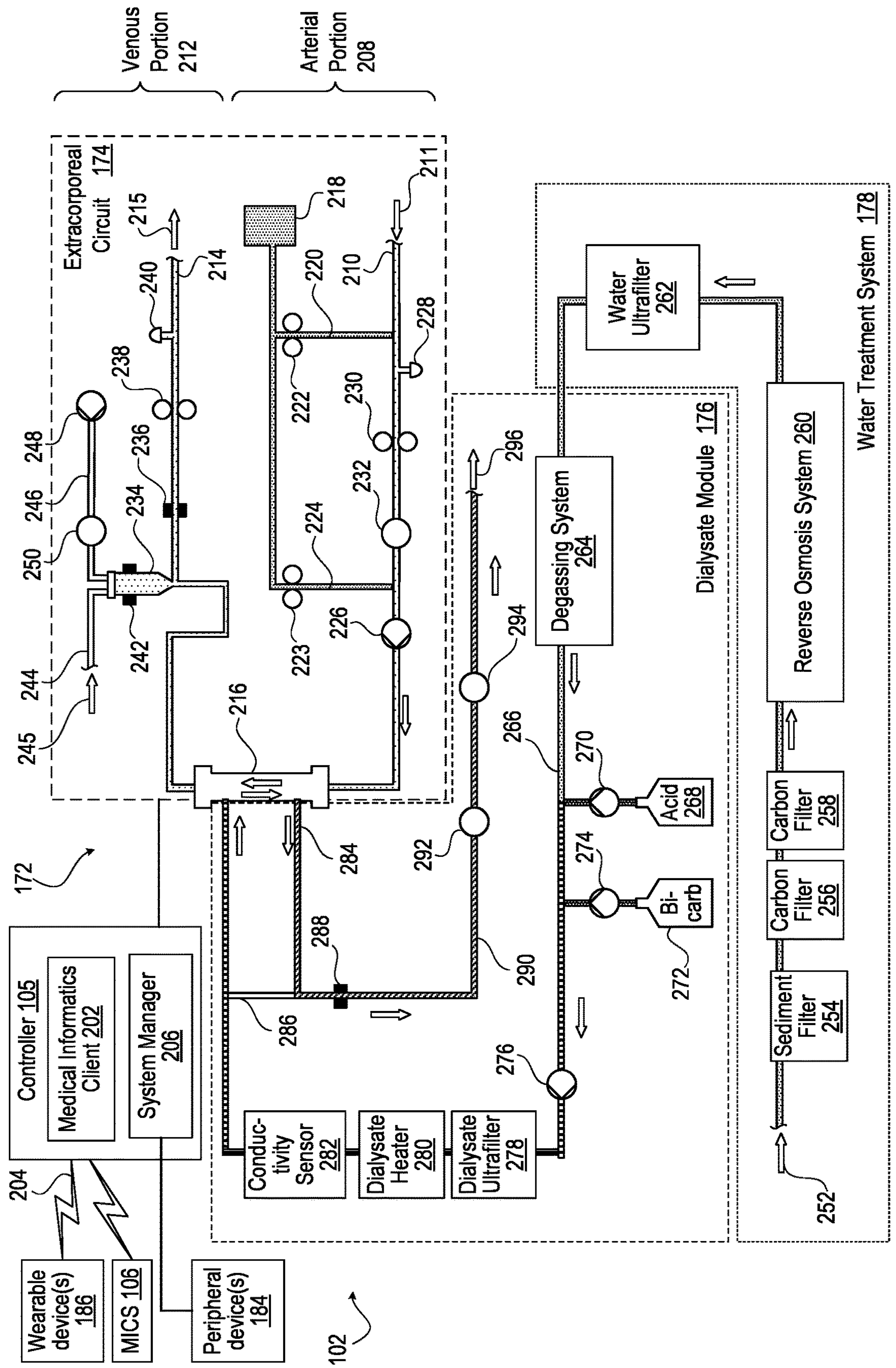
FIG. 2 is a diagrammatic illustration of the exemplary controller and fluidic system of the disclosed system of FIG. 1A.

FIG. 2 is a diagrammatic illustration of exemplary controller 105 and fluidics system 172 of dialysis device 102. Controller 105 includes medical informatics client 202 that is embedded software capable configuring dialysis device 102 to communicate, such as via wireless channel 204, with MICS 106 (FIG. 1A). Controller 105 includes system manager 206 for interfacing with sensors and controls of the fluidics system 172. Extracorporeal circuit 174 includes arterial portion 208 having first line 210 that receives unfiltered or untreated blood 211 from patient 104 (FIG. 1A) and a venous portion 212 having second line 214 that returns filtered or treated blood 215 to the patient 104 (FIG. 1A). Dialyzer 216 receives the blood from first line 210 for filtering and returns filtered or treated blood to second line 214. Arterial portion 208 includes additional components that interact with first line 210. Saline bag 218 can provide saline through first saline line 220 that is in fluid communication with an upstream portion of first line 210 and that is controlled by first pinch valve 222. Saline bag 218 can also provide saline through second saline line 224 that is in fluid communication with first line 210 that is upstream of blood pump 226 and downstream of arterial infusion port 228, arterial pinch valve 230, and arterial pressure sensor 232, as listed from upstream to downstream. Second saline line 224 may be controlled by second pinch valve 223. Venous portion 212 includes additional components that are listed in downstream order from dialyzer 216: accumulation vessel 234, air sensor 236, venous pinch valve 238, and venous infusion port 240. Accumulation vessel 234 includes level sensor 242, infusion line 244 to receive fluids 245, and adjustment line 246 fed by level adjust pump 248 and monitored by venous pressure sensor 250.

To provide filtering or treatment flow through dialyzer 216, water treatment system 176 provides ultrafiltered water to dialysate module 178 that in turn passes dialysate downward through dialyzer 216. In one or more embodiments, dialysate module 178 can be used to treat blood by transferring ultrapure dialysate through dialyzer 216 into the blood, reducing requirements for use of bagged saline. Blood flow through dialyzer 216 is in a reverse direction from arterial portion 208 to venous portion 212 of extracorporeal circuit 174. Incoming water 252 is directed in turn through sediment filter 254, first and second carbon filters 256 and 258, reverse osmosis system 260, and water ultrafilter 262 of the water treatment system 176. The ultrafiltered water pass through degassing system 264 of dialysate module 178 and to dialysate mixing line 266. Acid 268 is selectively injected into dialysate mixing line 266 via acid pump 270 and bicarbonate 272 is then selectively injected into dialysate mixing line 266 by bicarb pump 274. Dialysate pump 276 moves the dialysate on through dialysate ultrafilter 278, dialysate heater 280, and conductivity sensor 282. Dialysate mixing line 266 terminates at dialyzer 216. The used dialyzer exits dialyzer 216 via used dialyzer return line 284. Bypass line 286 is in fluid communication between dialyzer mixing line 266 and used dialyzer return line 284. Flow from bypass line 286 and used dialyzer return line 284 continues through drain line 288 that passes through blood leak detector 290, dialysate pressure sensor 292, and used dialysate pump 294 to exit to drain 296.

Figure 3:
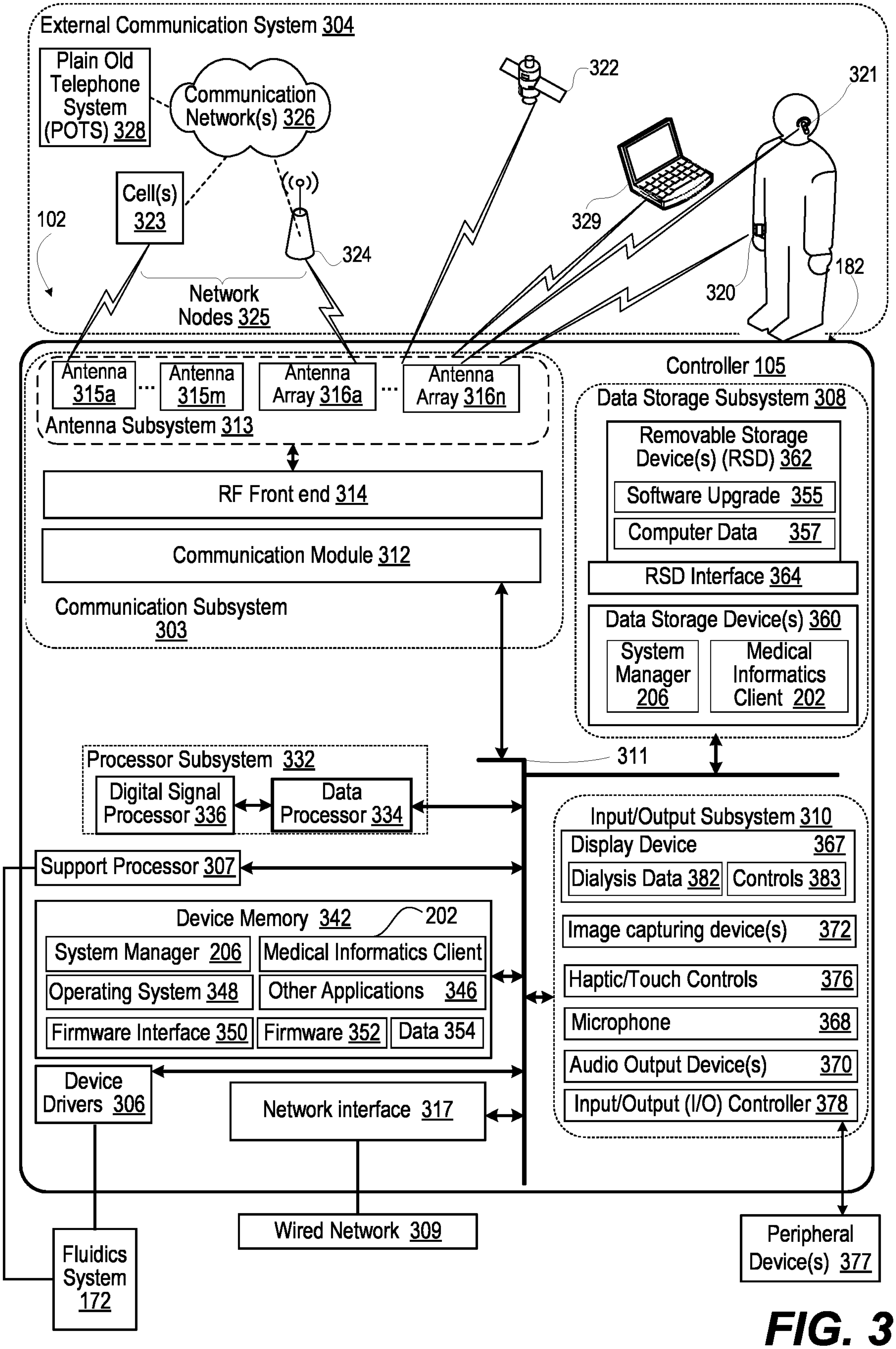
FIG. 3 is a diagrammatic illustration of the exemplary controller of FIG. 2 that may be used to manage the environment of FIG. 1A.

FIG. 3 is a diagrammatic illustration of exemplary controller 105, managed by controller 105, executes system manager 206 that manages dialysis device 102 and executes the medical informatics client 202 that configures over-the-air (OTA) communication subsystem 303 to communicate with MICS 106 (FIG. 3). System manager 206 can use device drivers 306 and support processor 307 to poll sensors or drive actuators of fluidics system 172 that configure or reconfigure operation of fluidics system 172. Referring now to the specific component makeup and the associated functionality of the presented components, controller 105 includes OTA communication subsystem 303 that communicates with external OTA communication system 304. Controller 105 can also use network interface 317 to wired network 309 (e.g., local access network (LAN)). Controller 105 provides computing and data storage functionality in support of OTA communication with external OTA communication system 304, as well as other functions, with processor 105, data storage subsystem 308, and input/output (I/O) subsystem 310 that are communicatively coupled via system interlink 311.

OTA communication subsystem 303 includes communication module 312 that encodes data for transmission and decodes received data according to an applicable communication protocol for OTA communication over antenna subsystem 313. OTA communication subsystem 303 includes front end(s) 314 that transceive information and data with external OTA communication system 304 via antennas 315*a*-315*n* for lower frequency bands and antenna array modules 316*a-b* for mounted within device housing 182.

In one or more embodiments, controller 105, via OTA communication subsystem 303, can perform multiple types of OTA communication with external OTA communication system 304. OTA communication subsystem 303 can communicate with one or more personal access network (PAN) devices such as via Bluetooth wireless link. Smart watch 320 and earphone 321 are examples of PAN devices. OTA communication subsystem 303 can also communicate with global positioning system (GPS) satellites 322, cellular nodes 323, and wireless local access network (WLAN). Cellular and wireless access can be generally referred to as connecting with network nodes 325 that communicate with one or more private or public communication networks 326, which can include a plain old telephone system (POTS) 328. OTA communication subsystem 303 can form an ad hoc network with user device 329.

Controller 105 controls the communication, user interface, and other functions and/or operations of dialysis device 102. These functions and/or operations include, but are not limited to including, application data processing and signal processing. Controller 105 may use hardware component equivalents for application data processing and signal processing. For example, controller 105 may use special purpose hardware, dedicated processors, general purpose computers, microprocessor-based computers, micro-controllers, optical computers, analog computers, dedicated processors and/or dedicated hard wired logic. As utilized herein, the term "communicatively coupled" means that information signals are transmissible through various interconnections, including wired and/or wireless links, between the components. The interconnections between the components can be direct interconnections that include conductive transmission media or may be indirect interconnections that include one or more intermediate electrical components. Although certain direct interconnections are illustrated in FIG. 3, it is to be understood that more, fewer, or different interconnections may be present in other embodiments.

Controller 105 includes processor subsystem 332 that executes program code to provide functionality of controller 105. Processor subsystem 332 includes one or more central processing units (CPUs) ("data processor") 334. Processing subsystem 332 can include a digital signal processor (DSP) 336 that can analyze treatment data received from sensors. Controller 105 includes system memory 342 for containing actively used program code and data. System memory 342 can include therein a plurality of such program code and modules, including applications, such as medical informatics client 202, system manager 206, and other applications 346. System memory 342 can also include operating system (OS) 348, firmware interface 350 such as basic input/output system (BIOS) or Uniform Extensible Firmware Interface (UEFI), and platform firmware (FW) 352. These software and/or firmware modules have varying functionality when their corresponding program code is executed by processor subsystem 332 or secondary processing devices such as support processor 307 within controller 105. Data 354 is stored in system memory 342, which includes PHI, treatment data, machine data, etc.

Data storage subsystem 308 provides nonvolatile storage accessible to controller 105. For example, data storage subsystem 308 can provide medical informatics client 202, the system manager 206, and a large selection of other applications 346 that can be loaded into system memory 342. Local data storage device(s) 360 can include hard disk drives (HDDs), optical disk drives, solid state drives (SSDs), etc. In one or more embodiments, removable storage device (RSD) 362 that is received in RSD interface 364 is a computer readable storage device, which can be referred to as non-transitory. RSD 362 can be accessed by controller 105 to provision controller 105 with program code that when executed by controller 105 provides the functionality to controller 105 to perform aspects of the present disclosure. For example, RSD 362 can provide software upgrades 355 and computer data 357 (e.g., settings) to provision the controller 105 as an alternative to network provisioning.

I/O subsystem 310 provides input and output devices, such as for enabling user inputs, presenting audiovisual content, or monitoring external audio output. In one or more embodiments, I/O subsystem 310 includes a display device 367, microphone 368, at least one internal audio output device or speaker 370, image capturing device or camera 372, tactile/haptic control 376, and input/output (I/O) controller 378. Microphone 368 can monitor remote audio output 380 from a user. At least one internal speaker 370 can locally produce a local audio output such as alerts. Image capturing device 372 can receive user gestures, faces for facial recognition, and other image data. Display device 367 can present dialysis data 382 and present controls 383 to solicit user inputs. Tactile/haptic control 376 can provide an interface such as for braille reading or manual inputs. I/O subsystem 310 can be wholly or substantially encompassed by device housing 182 or be connected via I/O controller 378 as a peripheral device 377.

Figure 4:
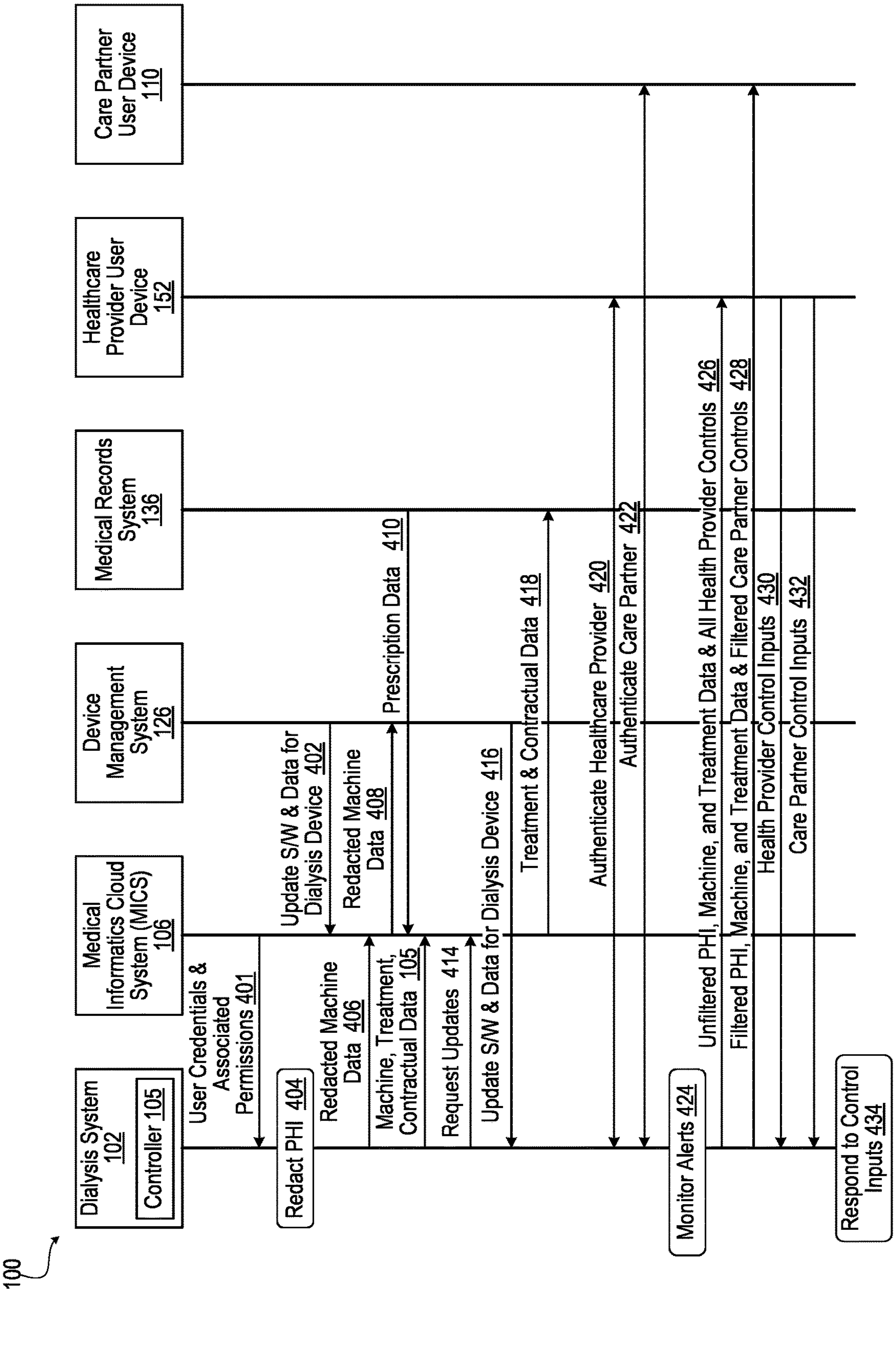
FIG. 4 is a timing diagrammatic illustration performed by the disclosed system of FIG. 1A.

FIG. 4 is a timing diagrammatic illustration performed by dialysis system 100. In an example, dialysis system 100 includes interactions between controller 105 of dialysis device 102, MICS 106, device management system 126, medical records system 136, healthcare provider user device 152, and care partner user device 110. Dialysis device 102 is being used in an ongoing dialysis treatment program for patient 104 (FIG. 1A). MICS 106 is provisioned with public authentication credentials for each stakeholder and transmits these credentials to controller 105 as indicated at line 401. Device management system 126 provisions MICS 106 with software, software upgrades, and configuration data for a population of dialysis devices 102 as indicated at line 402. In one or more embodiments, controller 105 redacts PHI from machine data and other data (block 404). Then controller 105 transmits the redacted machine data and other data to MICS 106 as indicated at line 406. MICS 106 transmits the redacted machine data and other data to device management system 126 for maintenance analysis as indicated at line 408. Medical records system 136 can transmit prescription data to MICS 106 as indicated at line 410. Controller 105 can transmit updates on machine, treatment and contractually-related data as requested or as initiated by controller 105 to MICS 106 as indicated at line 412. Periodically, controller 105 can request software and configuration data updates from MICS 106 as indicated at line 414. MICS 106 responds by transmitting the requested software and configuration data updates to controller 105 as indicated at line 416. MICS 106 can periodically update medical records system 136 with treatment and contractually-related information as indicated at line 418.

In one or more embodiments, MICS 106 can act as an intermediary for real-time data necessary for monitoring and control of dialysis device 102. In one or more embodiments to reduce data latency, controller 105 communicates with stakeholders directly, depicted as via user devices 110, 152. Controller 105 authenticates healthcare provider 150 (FIG. 1A) that is using user device 152 as indicated at line 420. Controller 105 authenticates care partner 108 (FIG. 1A) that is using user device 110 as indicated at line 422. During an active dialysis treatment, controller 105 monitors for control inputs from user devices 110, 152 and monitors alerts (block 424). Controller 105 transmits unfiltered PHI, machine, and treatment data and all health provider controls to user device 152 as indicated at line 426. In one or more embodiments, healthcare provider 150 (FIG. 1A) is on call and the communication session is initiated in response to an alert. Controller 105 transmits filtered PHI, machine, and treatment data and care partner controls to user device 110 as indicated at line 428. In one or more embodiments, care partner 108 (FIG. 1A) presumed to be in proximity to dialysis device 102 and the communication session is initiated in response to an alert that is not handled within a certain time limit at controller 105. In one or more embodiments, controller 105 can determine that care partner 108 (FIG. 1A) is not in proximity to controller 105 based on sensor readings or a control setting. Controller 105 receives health provider control inputs as indicated at line 430. Controller 105 receives care partner control inputs as indicated at line 432. Controller 105 responds to control inputs (block 434).

Figure 5A:
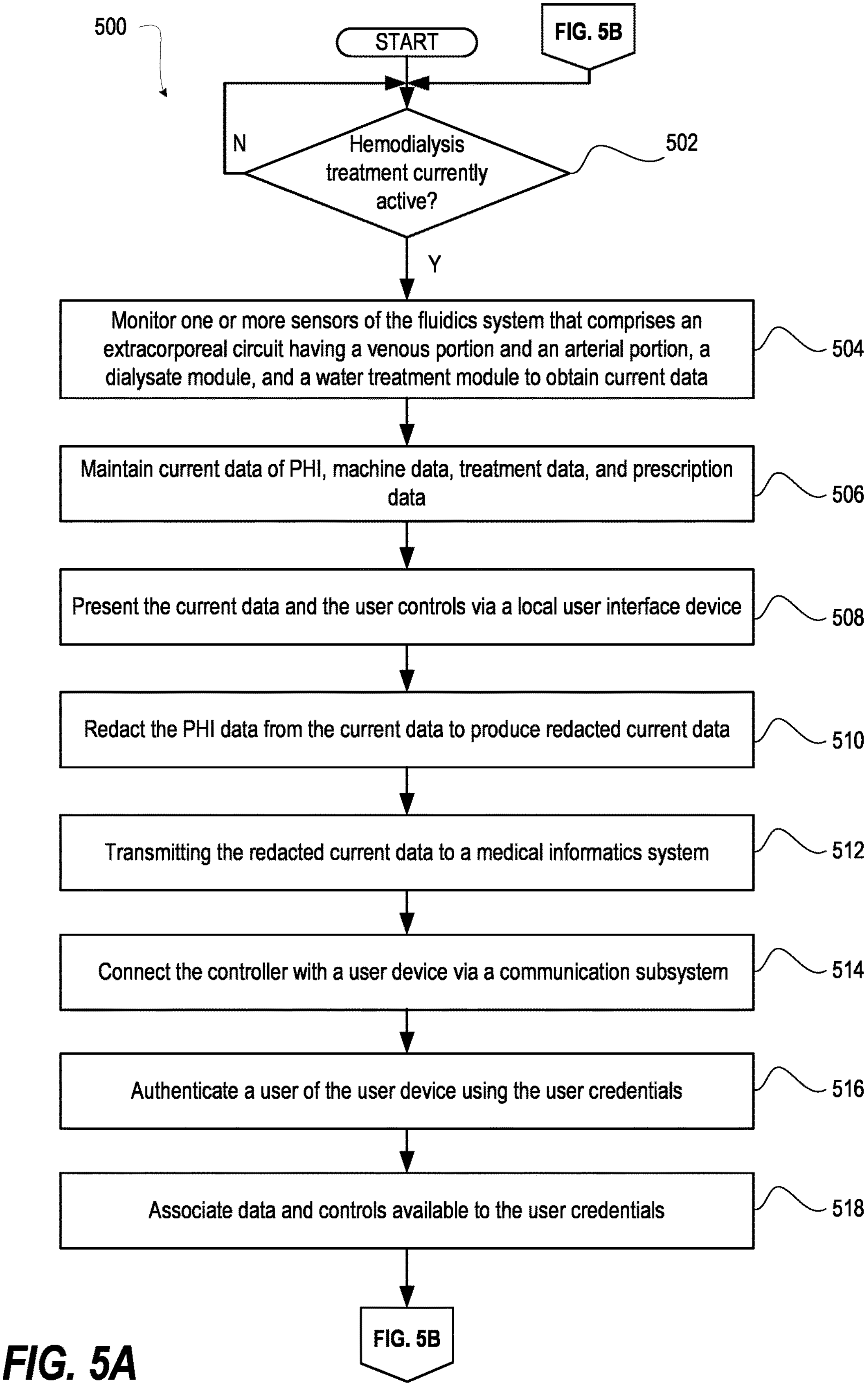
FIG. 5A is a flowchart depicting an exemplary disclosed method that may be performed by the disclosed system of FIG. 1A.
Figure 5B:
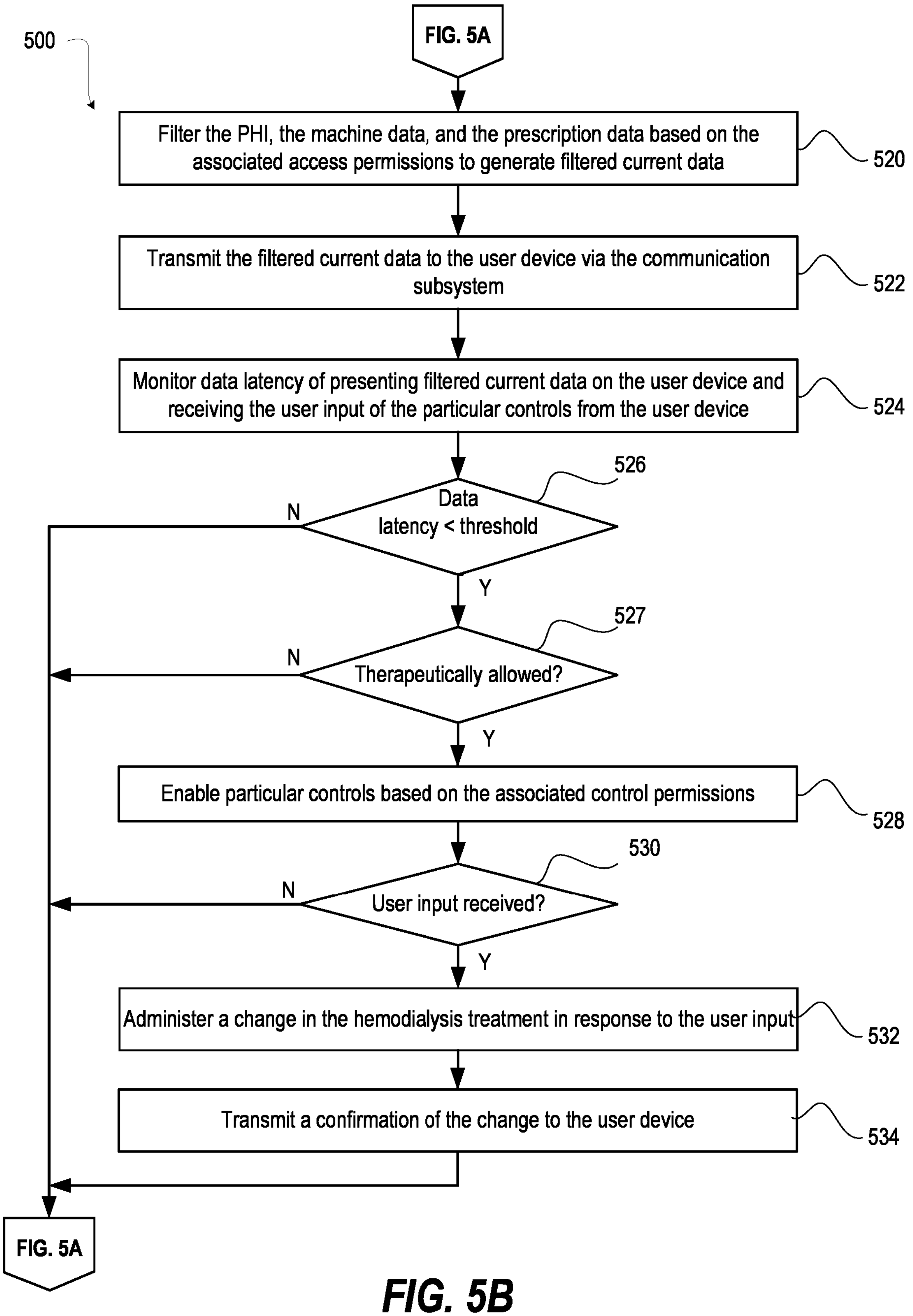
FIG. 5B is a continuation of flowchart 5A depicting an exemplary disclosed method that may be performed by the disclosed system of FIG. 1A.

FIGS. 5A-5B are a flowchart depicting an exemplary disclosed method 500 that may be performed by the dialysis system 100. In one or more embodiments, the method 500 is performed by controller 105 (FIG. 1A). Components referenced in FIGS. 5A-5B having the same name as described above in FIGS. 1A-1D and 2-4 can be similar or identical components. With reference to FIG. 5A, method 400 includes determining whether a dialysis treatment is currently active (decision block 502). In response to determining that the dialysis treatment is not currently active, method 500 returns to block 502. In response to determining that the dialysis treatment is currently active, method 500 includes monitoring one or more sensors of the fluidics system that comprises an extracorporeal circuit having a venous portion and an arterial portion, a dialysate module, and a water treatment module to obtain current data (block 504). Method 500 includes maintaining the current data of PHI, machine data, treatment data, and prescription data (block 506). Method 500 includes presenting the current data and the user controls via a local user interface device (block 508). Method 500 includes redacting the PHI data from the current data to produce redacted current data (block 510). In one or more embodiments, a screen share of the local user interface is redacted by blanking out particular portions of the display area that are assigned to PHI. Method 500 includes transmits the redacted current data to a medical informatics system (e.g., MICS 106 of FIG. 1A) (block 512). Method 500 includes connecting the controller with a user device via a communication subsystem (block 514). In one or more embodiments, the user device initiates a communication session. In one or more embodiments, the controller initiates the communication session, such as in response to the beginning of the treatment or in response to an alert. Method 500 includes authenticating a user of the user device using the user credentials (block 516). Method 500 includes associating data and controls available to the user credentials (block 518). In an example, the filtering is appropriate for a healthcare professional. In another example, the filtering is appropriate for a care partner.

With reference to FIG. 5B, method 500 includes filtering the PHI, the machine data, and the prescription data based on the associated access permissions to generate filtered current data (block 520). Method 500 includes transmitting the filtered current data to the user device via the communication subsystem (block 522). Method 500 includes monitoring data latency of presenting filtered current data on the user device and receiving the user input of the particular controls from the user device (block 524). Method 500 includes determining whether the data latency is less than threshold time (decision block 526). In response to determining that the latency is not less than the threshold time, then method 500 returns to block 502 (FIG. 5A). In response to determining that the latency is less than the threshold time, method 500 includes determining whether the particular controls are therapeutically allowed (block 527). Certain rules can be implemented to avoid certain reconfigurations of the fluidics system that could lead to injury of the patient or to damage to the equipment. Similarly, certain rules can be implemented that prompt reconfiguring the fluidics system to mitigate a current situation that could injure the patient or damage the equipment. As an example, for a particular patient, sensed parameters of the fluidics system and patient's vascular system should be within an acceptable range. The acceptable range can be therapeutically defined for the patient. The acceptable range can be defined for effective and reliable operation of the dialysis device. A therapeutically allowed care partner control may be one of: (i) maintain operation of the fluidics system within an acceptable range; or (ii) reconfigure operation of the fluidics system toward the acceptable range. As an example, the pressures exerted by the dialyzer and the blood flow through the dialyzer need to be within acceptable ranges for successful operation. As an additional example, blood pressures and blood flow rates at the fluidics interfaces between the dialysis device and the patient's vascular system need to be within acceptable ranges to avoid pain and stress to the patient.

In response to determining that the particular controls are not therapeutically allowed, method 500 returns to block 502 (FIG. 5A). In response to determining that the particular controls are therapeutically allowed, method 500 includes enabling particular controls based on the associated control permissions (block 528). Method 500 includes determining whether a user input to the particular controls is received (decision block 530). In response to not receiving a user input, method 500 returns to block 502 (FIG. 5A). In response to receiving a user input, method 500 includes administering a change in the dialysis treatment in response to the user input (block 532). Method 500 includes transmitting a confirmation of the change to the user device (block 534). Then method 500 returns to block 502 (FIG. 5A).

All publications and patent applications mentioned in this specification are herein incorporated by reference to the same extent as if each individual publication or patent application was specifically and individually indicated to be incorporated by reference.

It will be apparent to those skilled in the art that various modifications and variations may be made to the disclosed system. Other examples will be apparent to those skilled in the art from consideration of the specification and practice of the disclosed system. It is intended that the specification and examples be considered as illustrative only, with a true scope being indicated by the following claims and their equivalents.

What is claimed is:

1. A dialysis system comprising:
- a fluidics system configured to perform a dialysis treatment session for a patient, the fluidics system comprising:
  - at least one sensor that senses a corresponding at least one parameter;
- a dialyzer; and
  - at least one dialysis actuator that configures fluid flow through the fluidics system;
- a communication subsystem configured to communicatively connect to one or more remote user devices; and
- a controller communicatively coupled to the fluidics system and the communication subsystem, the controller configured to:
  - operate the fluidics system to perform the dialysis treatment session;
  - maintain data associated with the fluidics system, the data comprising data types of: (i) patient health information (PHI); (ii) de-identified health information; and (iii) non-health information;
  - identify access rights associated with a first credential used by a first remote user device, the access rights comprising levels of (i) access to all data types; and (ii) access to a subset of data types;
  - communicate one or more of the data types to the first remote user device according to the access rights;
  - identify control privileges of the fluidic system associated with the first credential used by the first remote user device, the control privileges comprising levels of (i) no control of the fluidic system; (ii) a subset of controls of the fluidic system; and (iii) all controls of the fluidic system; and
  - in response to receiving from the first remote user device a control input comprising at least a portion of a prescription attributed to a patient identifier:
    - determine whether the first remote user device has the corresponding control privileges associated with the control input; and
    - configure the fluidics system in response to the control input according to the corresponding control privileges,
- wherein de-identified health information comprises health information that has had patient identifying information removed from the health information.

2. The dialysis system of claim 1, wherein the controller is further configured to:
- access the prescription attributed to a patient identifier via the communication subsystem; and
- configure the fluidics system according to the prescription to perform the dialysis treatment session.

3. The dialysis system of claim 1, wherein the fluidics system further comprises:
- an extracorporeal circuit comprising:
- an arterial portion configured to receive untreated blood from the patient;
- a venous portion configurable to return treated blood to the patient;
- a dialysate module comprising the dialyzer that treats the untreated blood; and
- a water treatment module that provides filtered water to the dialysate module.

4. The dialysis system of claim 1, wherein the controller is further configured to:
- monitor the at least one sensor and respective states of the at least one dialysis actuator to determine a current state of the dialysis treatment session;
- determine whether the control input is therapeutically allowed based on the current status of the dialysis treatment session;
- in response to determining that the current state of the dialysis treatment session comprises at least one fluidics parameter being outside of an acceptable range:
  - associate the control input with a therapeutic response to the at least one fluidics parameter being outside of the acceptable range; and
  - communicate a control recommendation to the first remote user device in response to determining that the control level associated with the first remote user device allow selection of the control recommendation.

5. The dialysis system of claim 4, wherein:
- the at least one sensor senses the corresponding at least one parameter that is related to blood flow rate;
- the at least one dialysis actuator comprises a blood pump positioned to move untreated blood of the patient through the dialyzer at a defined blood flow rate; and
- the controller actuates a pump rate of the blood pump to adjust the blood flow rate toward the acceptable range.

6. The dialysis system of claim 4, wherein:
- the at least one sensor comprises one or more of: (i) a blood pressure sensor configured to measure the at least one fluidics parameter comprising a blood pressure of the patient; and (ii) a blood volume sensor configured to determine the at least one fluidics parameter comprising available blood volume of the patient;
- the at least one dialysis actuator is configured to selectively allow at least one of: (i) a saline bolus; and (ii) an ultrapure dialysate to be infused with the blood of the patient;
- the at least one fluidics parameter is based on at least one of an arterial pressure value detected by an arterial pressure sensor and a venous pressure value detected by a venous pressure sensor; and
- the controller actuates the at least one dialysis actuator to infuse the at least one of: (i) a saline bolus; and (ii) the ultrapure dialysate to adjust the at least one fluidics parameter toward the acceptable range.

7. The dialysis system of claim 4, wherein:
- the at least one sensor comprises one or more of: (i) a blood pressure sensor configured to measure the at least one fluidics parameter comprising blood pressure of the patient; and (ii) a blood volume sensor configured to determine the at least one fluidics parameter comprising available blood volume of the patient;
- the at least one dialysis actuator comprises a dialysate pump positioned to move dialysate through the dialyzer at a dialysate flow rate;
- the prescription comprises at least one of a fluid removal rate goal and a fluid removal amount goal that is related to a pump rate of the dialysate pump and related to a duration of the dialysis treatment session; and
- the controller adjusts the pump rate of the dialysate pump and correspondingly adjusts at least one of the fluid removal rate goal and the fluid removal amount goal to cause an adjustment of the at least one parameter toward the acceptable range.

8. The dialysis system of claim 4, wherein the controller is further configured to:

transmit a report to the first remote user device indicating successful configuration of the fluidics system in response to the control input being both allowed therapeutically and according to control level; and transmit a report to the first remote user device indicating unsuccessful configuration of the fluidics system in response to the control input being one or more of not allowed therapeutically or not allowed according to the control level of control privileges associated with the first credential.

9. The dialysis system of claim 1, wherein the controller is further configured to transmit one or more signals comprising de-identified health information to the first remote user device by:

generating a graphical user interface of the dialysis treatment session that depicts both PHI and de-identified health information in one or more spatially-defined field locations of the graphical user interface;

determining which spatially-defined field locations are reserved for PHI;

altering the graphical user interface to block the spatially-defined field locations reserved for PHI; and communicating the altered graphical user interface to the first remote user device.

10. The dialysis system of claim 1, wherein the controller is further configured to:

in response to determining that the access rights comprise notification of the dialysis treatment session:

communicate a first report indicating initiation of the dialysis treatment session to the first remote user device in response to beginning the dialysis treatment session; and communicate a second report indicating termination of the dialysis treatment session to the first remote user device in response to ending the dialysis treatment session.

11. The dialysis system of claim 1, wherein the controller is further configured to:

in response to determining that the current state of the dialysis treatment session comprises at least one fluidics parameter being outside of an acceptable range:

associate the control input with a therapeutic response to the at least one fluidics parameter being outside of the acceptable range;

identify a particular remote user device of the one or more remote user devices having control privileges associated with the control input;

connect with the particular remote user device using the communication subsystem; and communicate a control recommendation to the particular remote user device.

12. The dialysis system of claim 1, wherein the access rights associated with the first credential used by the first remote user device are based on a contractual relationship, a fiduciary relationship, and/or a duty of care for the patient.

13. The dialysis system of claim 1, wherein the data types further comprise real-time dialysis treatment data.

14. A non-transitory computer-readable medium storing program instructions that, when executed using one or more processors, cause the one or more processors to:

operate a fluidics system to perform a dialysis treatment session for a patient, the fluidics system comprising at least one sensor that measures a corresponding at least one parameter and at least one dialysis actuator that configures fluid flow through the fluidics system;

maintain data associated with the fluidics system, the data comprising data types of: (i) patient health information (PHI); (ii) de-identified health information; and (iii) non-health information;

identify access rights associated with a first credential used by a first remote user device, the access rights comprising levels of (i) access to all data types; and (ii) access to a subset of data types;

communicate one or more of the data types to the first remote user device according to the access rights;

identify control privileges of the fluidic system associated with the first credential used by the first remote user device, the control privileges comprising levels of (i) no control of the fluidic system; (ii) a subset of controls of the fluidic system; and (iii) all controls of the fluidic system; and in response to receiving a control input from a first remote user device via a communication subsystem, the control input comprising at least a portion of a prescription attributed to a patient identifier:

determine whether the first remote user device has the corresponding control privileges associated with the control input; and configure the fluidics system in response to the control input according to the corresponding control privilege, wherein de-identified health information comprises health information that has had patient identifying information removed from the health information.

15. A dialysis system comprising:

a fluidics system configured to perform a dialysis treatment session for a patient, the fluidics system comprising:

at least one sensor that senses a corresponding at least one parameter;

a dialyzer; and at least one dialysis actuator that configures fluid flow through the fluidics system;

a communication subsystem configured to communicatively connect to one or more remote user devices; and a controller communicatively coupled to the fluidics system and the communication subsystem, the controller configured to:

operate the fluidics system to perform the dialysis treatment session;

identify access rights associated with a first credential used by a first remote user device, the access rights comprising levels of (i) access to all data types; and (ii) access to a subset of data types;

communicate one or more of the data types to the first remote user device according to the access rights;

identify control privileges of the fluidic system associated with the first credential used by the first remote user device, the control privileges comprising levels of (i) no control of the fluidic system; (ii) a subset of controls of the fluidic system; and (iii) all controls of the fluidic system;

associate control privileges with the first credential based on the at least one parameter sensed by the at least one sensor; and in response to receiving from the first remote user device a control input comprising at least a portion of a prescription attributed to a patient identifier:

determine whether the first remote user device has the corresponding control privileges associated with the control input; and configure the fluidics system in response to the control input being according to the corresponding control privileges.

16. The dialysis system of claim 15, wherein the controller is further configured to associate control privileges with the first credential based on a predetermined treatment schedule.

17. The dialysis system of claim 15, wherein the subset of controls level of the control privileges comprises: (i) therapeutically allowed controls; and (ii) maintenance actions permitted only while the session is not operated.

* * * * *